US008229757B2

(12) United States Patent
Paradis et al.

(10) Patent No.: US 8,229,757 B2
(45) Date of Patent: Jul. 24, 2012

(54) SYSTEM AND METHOD FOR MANAGING HEALTH CARE COMPLEXITY VIA AN INTERACTIVE HEALTH MAP INTERFACE

(75) Inventors: Janet Paradis, Windsor Locks, CT (US); Michael Shaw, Horsham, PA (US); Frederick B. Barclay, Jr., Chester, CT (US); Amy Cueva, Barrington, NH (US)

(73) Assignee: Aetna Inc., Hartford, CT (US)

( * ) Notice: Subject to any disclaimer, the term of this patent is extended or adjusted under 35 U.S.C. 154(b) by 1011 days.

(21) Appl. No.: 11/865,538

(22) Filed: Oct. 1, 2007

(65) Prior Publication Data

US 2009/0089083 A1 Apr. 2, 2009

(51) Int. Cl.
*G06Q 40/00* (2012.01)
(52) U.S. Cl. .............................................. 705/2; 705/3
(58) Field of Classification Search ................ 705/2, 3
See application file for complete search history.

(56) References Cited

U.S. PATENT DOCUMENTS

| | | | |
|---|---|---|---|
| 4,905,163 | A | 2/1990 | Garber et al. |
| 6,169,997 | B1 | 1/2001 | Papierniak et al. |
| 2004/0128163 | A1* | 7/2004 | Goodman et al. ............. 705/2 |
| 2005/0120039 | A1 | 6/2005 | Amys et al. |
| 2007/0011026 | A1 | 1/2007 | Higgins et al. |
| 2007/0027722 | A1 | 2/2007 | Hasan et al. |
| 2008/0091463 | A1* | 4/2008 | Shakamuri ..................... 705/2 |

FOREIGN PATENT DOCUMENTS

WO PCT/US08/78317 12/2008

OTHER PUBLICATIONS

International Search Report and Written Opinion for PCT/US08/78317.
American Thoracic Society, "Standards for the Diagnosis and Management of Patients with COPD" obtained from the internet at http://www.thoracic.org/sections/copd/for-health-professionals/index.html on Jun. 1, 2007 (Copyright 2007).
Cnet News.com, "The Big Picture" obtained from the internet at http://news.com.com/ The+Big+Picture/2030-12_3-5843390.,html on Jun. 12, 2007 (Copyright 2007).

* cited by examiner

*Primary Examiner* — Luke Gilligan
*Assistant Examiner* — Maroun Kanaan
(74) *Attorney, Agent, or Firm* — Leydig, Voit & Mayer, Ltd.

(57) ABSTRACT

To empower a member to make informed health care decisions, a health care organization (HCO) graphically presents the member with a manageable closed universe of health care information via an online interactive visual interface. The online interactive interface comprises a custom category node display of member health care data based on analyzing the member profile in light of the overall health care data taxonomy built by the HCO. Upon identifying the subset of relevant health care data categories, HCO initiates the display of the identified categories by way of a dynamically linked category node interface. To enhance the member's understanding of the relationships between the category nodes, the HCO preferably employs a ring node topology by displaying the online interface as a closed network or map, such as by locating each category node along one or more closed, loop-shaped wireframes, which connect the interrelated categories.

20 Claims, 8 Drawing Sheets

SYSTEM AND METHOD FOR MANAGING HEALTH CARE COMPLEXITY VIA AN INTERACTIVE HEALTH MAP INTERFACE

FIELD OF THE INVENTION

This invention relates generally to the field of insurance and more specifically to the area of managing health care information.

BACKGROUND OF THE INVENTION

To successfully manage the wealth of information generated from interaction with a modern health care system, a patient must analyze a universe of data ranging from health condition and disease management, to benefits selection and financial planning related to projected health care expenses. For instance, a typical visit to a health care provider requires the patient to dissect the information from health condition pamphlets, explanation of benefits statements (EOB), patient invoices, and health savings account statements. Patients undergoing a long term treatment or having multiple forms of treatment related to different conditions and diseases must continuously wade through a universe of cryptic health care data to ensure that their current benefit levels and health savings account balances are adequate in light of the ongoing medical expenses.

Existing solutions have generally addressed the problem of centralized storage of health care information, but do little more than store that information and make it available to the patient for viewing. Therefore, it remains up to the patient to interpret the complex universe of health care data and to devise the relationships between various aspects of health care. However, the absence of easily understandable terminology makes it difficult to devise a cohesive health care plan that includes all aspects of health care—from health and benefit management to financial planning associated with health care expenses.

BRIEF SUMMARY OF THE INVENTION

To empower a health care plan member to make informed health care decisions, a health care organization (HCO) graphically presents the member with a manageable closed universe of health care information via an online interactive visual interface. The online interactive interface comprises a custom category node display of member health care data based on analyzing the member profile in light of an overall health care data taxonomy built by the HCO. Preferably, upon receiving member login information, the HCO identifies the member and analyzes the corresponding member profile to identify relevant health data categories among the plurality of health care data categories of the overall data taxonomy. Upon identifying the subset of relevant health care data categories, HCO initiates the display of the identified categories by way of a dynamically linked category node interface. In embodiments, the HCO displays at least some of the relevant categories of the health care data taxonomy directly, while creating custom groupings of other relevant categories.

Upon member login into the online interactive visual interface, the HCO identifies the health care data categories of the overall data taxonomy that are relevant to the member by performing one or more of the following analyses of the member profile: (a) analysis of the health conditions and medications data for diagnosed conditions, as well as potential undetected health risks and/or conditions, (b) analysis of claims for potential cost savings, such as through identifying whether a purchase of generic prescriptions and/or taking advantage of mail order pharmacy services may reduce the member's out-of-pocket costs, (c) identification of relevant HCO programs and resources, which the member is not currently taking advantage of, (d) identification of relevant health content data that needs to be presented to the member, and (e) financial analysis of the member profile to identify and suggest best use of member's benefits, as well as provide suggestions to reduce the member's health-based financial risk (for example, by suggesting an increase in the member's contribution to a tax-advantaged health care savings plan).

Once identified, the relevant health care category nodes are displayed for the member as an interactive visual category node map, wherein related category nodes are interconnected by wireframes to enhance the member's understanding of the relationships between the nodes and to provide a navigational aid with respect to the member's current position within the universe of his or her health care data. To enhance the member's understanding of the relationships between the category nodes, the HCO preferably employs a ring node topology by displaying the online interface as a closed network or map, such as by locating each category node along one or more closed, loop-shaped wireframes, which connect the interrelated categories. In an embodiment, the interactive category node map includes at least one category node (e.g., a parent node) which is expandable into one or more related subcategories (e.g., child and grandchild nodes). This allows the member to explore varying levels of complexity of his or her health care data by expanding or collapsing the category node display to and from the root node map. Preferably, the category node map dynamically reorients the node display depending upon the currently selected category. The online display further includes text and hyperlink content relating to the selected category.

In one aspect, a method is provided for graphically representing a subset of a plurality of health care data categories to a health care plan member via an online health care category node map, the method comprising (a) building a health care data taxonomy relating health care terminology to one or more of health care benefits terminology, health care-related financial terminology, health insurance terminology, and dental insurance terminology, (b) building and dynamically updating a member profile for the health care plan member, (c) storing the health care data taxonomy and the member profile in a database, (d) receiving an online member identification token associated with the health care plan member, (e) identifying the subset of the plurality of health care data categories based on correlating the health care data taxonomy with the member profile corresponding to the online member identification token, and (f) initiating a display of the online health care category node map, the display comprising a ring node topology for graphically indicating a relationship between adjacent health care category nodes within the subset, the online health care category node map capable of responding to member input for selecting a category node by orienting the ring node topology display around the selected category node, and wherein at least one category node in the online health care category node map comprises one or more subnodes corresponding to one or more health care data subcategories, (with at least one category node capable of expanding into the one or more subnodes responsive to member input.

In another aspect, a computer readable medium is provided having stored thereon computer executable instructions for graphically representing a subset of a plurality of health care data categories to a health care plan member via an online health care category node map, the instructions comprising (a) building a health care data taxonomy relating health care terminology to one or more of health care benefits terminology, health care-related financial terminology, health insurance terminology, and dental insurance terminology, (b) building and dynamically updating a member profile for the health care plan member, (c) storing the health care data taxonomy and the member profile in a database, (d) receiving an online member identification token associated with the health care plan member, (e) identifying the subset of the plurality of health care data categories based on correlating the health care data taxonomy with the member profile corresponding to the online member identification token, and (f) initiating a display of the online health care category node map, the display comprising a ring node topology for graphically indicating a relationship between adjacent health care category nodes within the subset, the online health care category node map capable of responding to member input for selecting a category node by orienting the ring node topology display around the selected category node, and wherein at least one category node in the online health care category node map comprises one or more subnodes corresponding to one or more health care data subcategories, with at least one category node capable of expanding into the one or more subnodes responsive to member input.

In yet another aspect, a system for graphically representing a subset of a plurality of health care data categories to a health care plan member via an online health care category node map, the system comprising a database for storing (a) a health care data taxonomy relating health care terminology to one or more of health care benefits terminology, health care-related financial terminology, health insurance terminology, and dental insurance terminology, and (b) a dynamic member profile for the health care plan member, a server for initiating a display of the online health care category node map, the server comprising memory having stored thereon computer executable instructions for (i) receiving an online member identification token associated with the health care plan member, (ii) identifying the subset of the plurality of health care data categories based on correlating the health care data taxonomy with the member profile corresponding to the online member identification token, and (iii) initiating the display of the online health care category node map, the display comprising a ring node topology for graphically indicating a relationship between adjacent health care category nodes within the subset, the online health care category node map capable of responding to member input for selecting a category node by orienting the ring node topology display around the selected category node, and wherein at least one category node in the online health care category node map comprises one or more subnodes corresponding to one or more health care data subcategories, with at least one category node capable of expanding into the one or more subnodes responsive to member input.

BRIEF DESCRIPTION OF THE DRAWINGS

While the appended claims set forth the features of the present invention with particularity, the invention and its advantages are best understood from the following detailed description taken in conjunction with the accompanying drawings, of which:

DETAILED DESCRIPTION OF THE INVENTION

The following examples further illustrate the invention but, of course, should not be construed as in any way limiting its scope.

Figure 1:
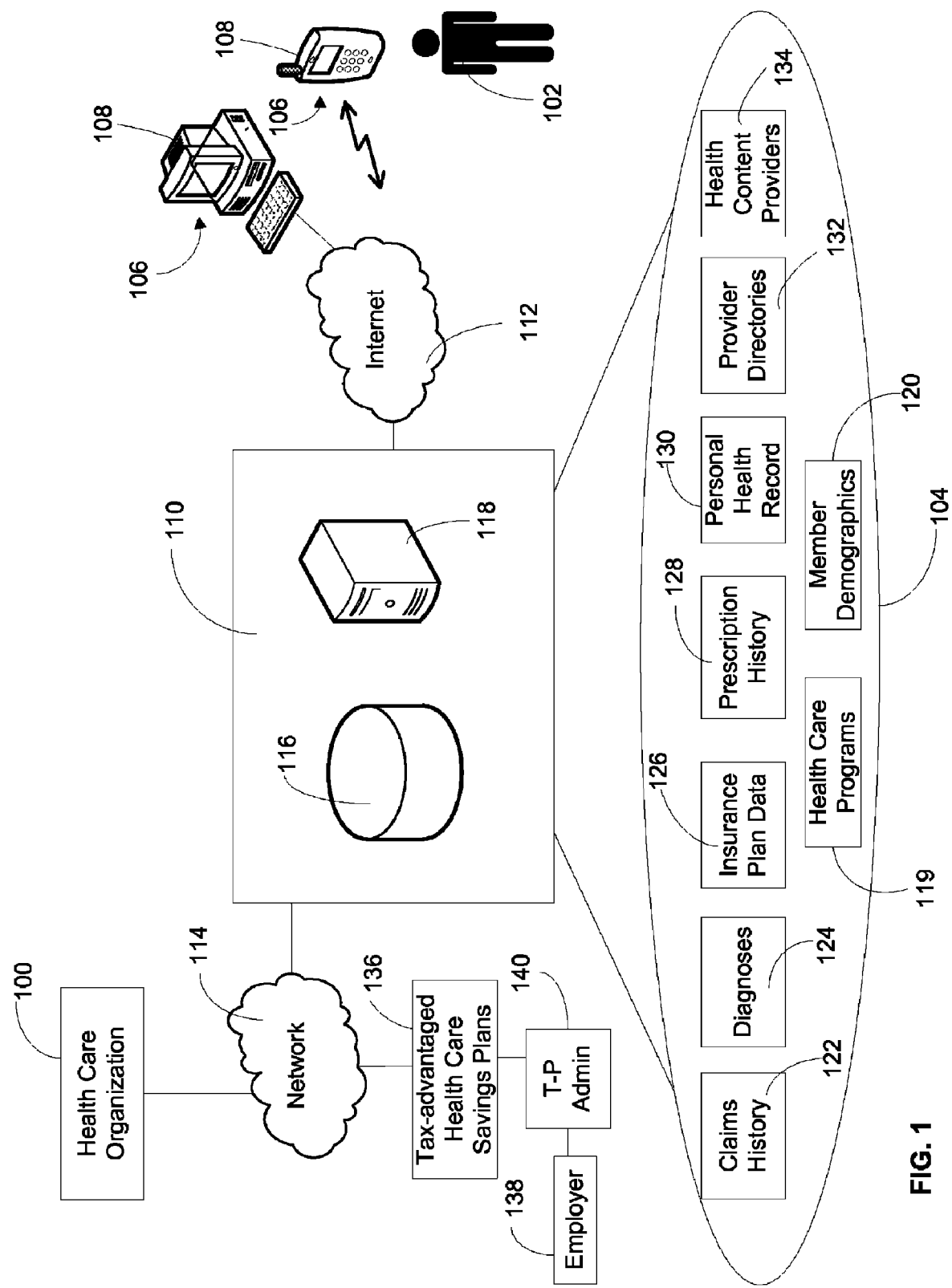
FIG. 1 is a diagram of an implementation of a system contemplated by an embodiment of the invention with reference to an overall health care organization environment.

Turning to FIG. 1, an implementation of a system contemplated by an embodiment of the invention is shown with reference to an overall health care organization environment. Preferably, the health care organization (HCO) 100 is a health insurance organization engaged in administering and underwriting individual and group health care coverage, including medical and dental plans, behavioral health and disease management programs, etc. To enable the plan member 102 to take full control of the vast universe of health care information 104, the HCO 100 presents the member 102 with a customized view of the health care information 104 via an online interactive visual interface 106, which the member 102 accesses via his or her personal computer 108 or another network-ready wired or wireless computing device, such as a mobile telephone or a PDA. The online interactive interface 106 comprises a categorized view of the health care information 104 collected and processed by the HCO 100 via a network-aware information storage and processing unit 110, which communicates with the member's personal computer or other interactive network interface device 108 via a network 112.

Preferably, the network 112 is a wide area network (WAN), such as the Internet, employing known communication and security/encryption protocols, such as TCP/IP and TLS/SSL, or the like. Alternatively or in addition, the network 112 includes a virtual private network (VPN) connectivity. In an embodiment, the HCO 100 manages the operation of the network-aware information storage and processing unit 110 via the network 114, such as a local area (LAN) or a WAN-type network. In one embodiment, the HCO 100 operates the network-aware information storage and processing unit 110 directly. Alternatively, the HCO 100 maintains a connection to the network-aware information storage and processing unit 110 via the network 114, while outsourcing the operation of the network-aware information storage and processing unit 110 to another entity. The network-aware information storage and processing unit 110 comprises one or more databases 116 connected to one or more information servers 118, each comprising a processor, computer memory, and other computer readable media. In an embodiment, the database 116 is part of the computer readable media of the information server 118. Alternatively, the database 116 resides on a separate computer and/or computer network.

To compile and analyze the health care information 104 at the network-aware information storage and processing unit 110, the HCO 100 collects health care programs data 119, member demographic data 120, claims history data 122, diagnoses data 124, insurance plan data 126 (including benefit types and corresponding benefits limits), prescription history data 128, and personal health record (PHR) data 130. In an embodiment, the PHR data 130 includes member-entered information received by the HCO 100 via an online personal health record that allows the member 102 to update his or her self-reported health conditions, over-the-counter medications, allergies, and other health care information which may not be otherwise available to the HCO 100 via claims processing. Additionally, the HCO 100 collects health care provider directory information 132, as well as information on the latest industry news and best practices from one or more health content providers 134. In the illustrated embodiment, the HCO 100 also communicates with one or more tax-advantaged health care savings plans 136 via a network 114. The tax-advantaged savings plans 136 include one or more of FSA, HSA, HRA, and MSA plans administered by an employer 138, either directly or via a third-party administrator 140. Alternatively, the HCO 100 administers, either directly or via a third-party administrator 140, one or more of the tax-advantaged plans 136.

Figure 2:
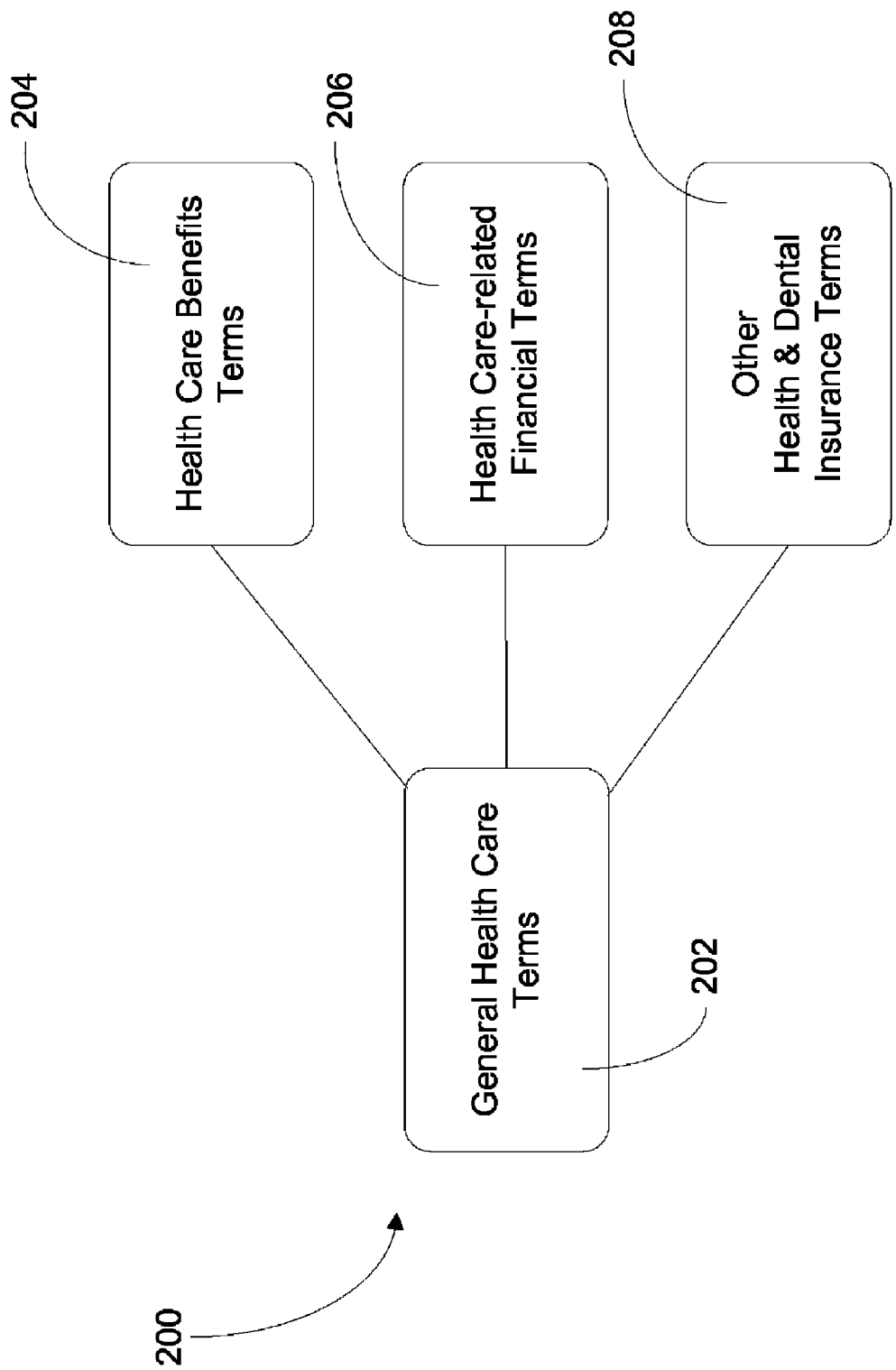
FIG. 2 is a diagram illustrating a health care data taxonomy comprising a plurality of related health care data categories, in accordance with an embodiment of the invention.

As illustrated in FIG. 2, in connection with collecting the health care information 104, the HCO 100 builds a health care data taxonomy 200 comprising a plurality of related health care data categories. Specifically, the health care data taxonomy 200 relates general health care terminology 202 to health care benefits terminology 204, health care-related financial terminology 206, as well as other health and dental insurance, diagnostic and claims terminology 208. Exemplary general health care terminology 202 comprises, without limitation: health diseases and conditions (e.g., heart disease, pregnancy), preventive care, heart attack prevention, eye care, smoking cessation, cholesterol control, blood sugar control, and weight management, among others. The HCO 100 correlates the foregoing general health care terminology with health care benefits terminology 204, including medical, Medicare and pharmacy benefits, well baby care benefits, preventive/physical exam benefits, ER, in-patient/out-patient benefits, behavioral health benefits, and disease management programs. Likewise, exemplary health care-related financial terminology 206 includes such terms as deductible, coinsurance, patient responsible balance (PRB), tax-advantaged plans, insurance discounts, and coordination of benefits, among others. Exemplary health and dental insurance terminology 208 includes inpatient/out-patient medical claims, explanation of benefits (EOB), diagnosis codes, pharmacy claims, and dental claims, among others.

Figure 3:
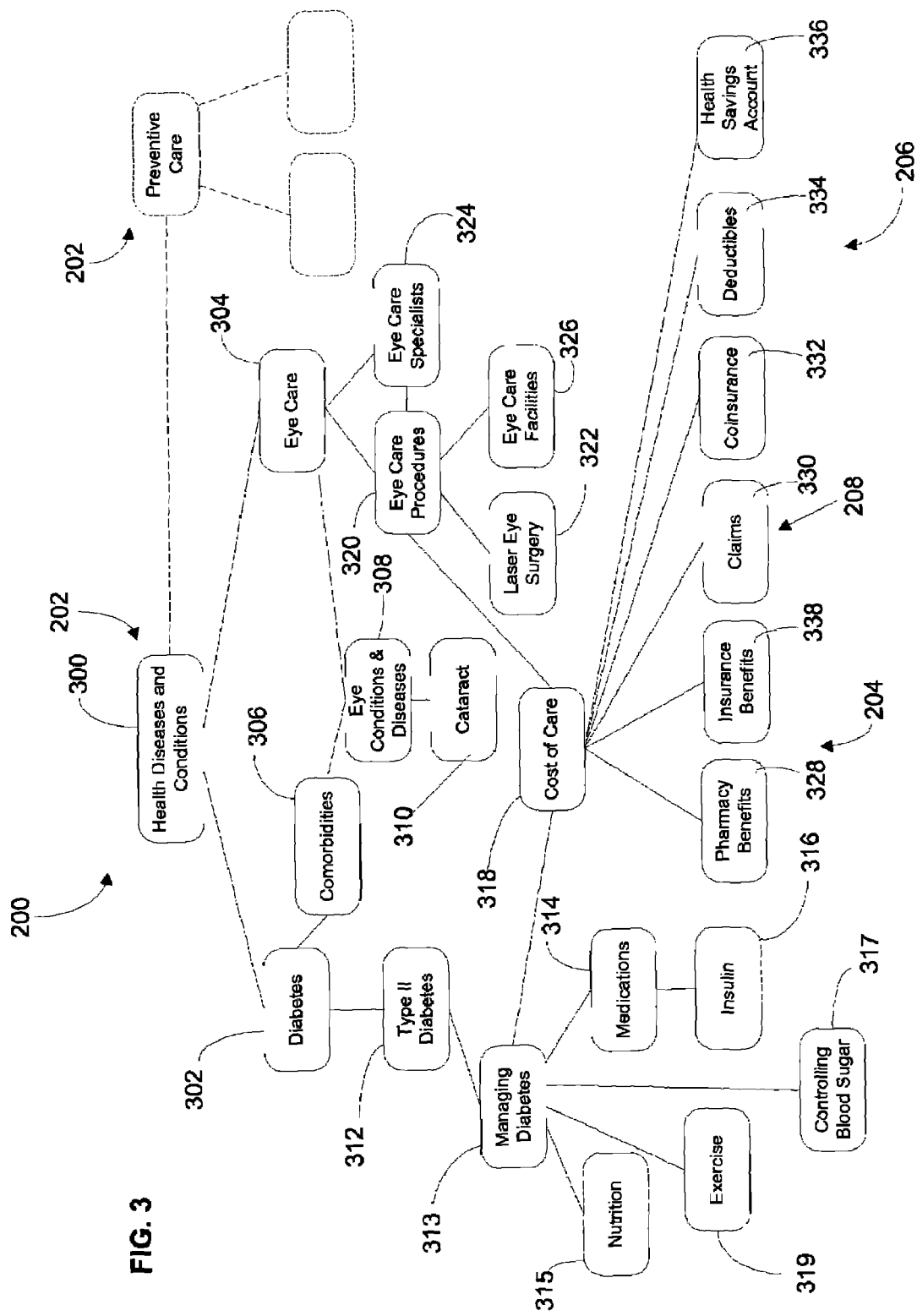
FIG. 3 is a diagram illustrating an embodiment of the data taxonomy of FIG. 2 in more detail with respect to general health care terminology relating to a health diseases and conditions category.

Turning to FIG. 3, an embodiment of the data taxonomy 200 is illustrated in more detail with respect to general health care terminology 202 relating to a health diseases and conditions category 300. The health care data taxonomy 200 comprises logical relationships between a plurality of health care data categories. For example, the diabetes and eye care subcategories 302, 304 are indirectly related via a comorbidities subcategory 306 when a member diagnosed with diabetes is at risk for developing an eye disease 308, such as cataract 310. Progressing further along the data taxonomy 200, a member diagnosed with Type II diabetes category 312, will require medications 314 (e.g., insulin 316) to manage 313 his or her Type II diabetes. The managing diabetes category 313, in addition to the medications subcategory 314, further includes nutrition, exercise, and controlling blood sugar subcategories 315, 317, 319. The managing diabetes category 313, in turn, relates to a cost of care category 318, which is also related to eye care procedures category 320 when the member needs to have laser eye surgery 322 performed by one of the eye care specialists under category 324 at a given eye care facility corresponding to a category 326. Progressing yet further along the illustrated portion of the health care data taxonomy 200, the general health care terminology 202, represented via the health diseases and conditions category 300, and health care benefits terminology 204, represented via the pharmacy benefits category 328 and insurance benefits category 338, are interrelated via the cost of care category 318 and preceding categories 302, 312, 313 or 304, 320. Similarly, the cost of care category 318 relates the health diseases and conditions category 300 to the claims category 330, representing the health and dental insurance terminology 208 of the overall data taxonomy 200. The cost of care category 318 also relates health diseases and conditions category 300 to the coinsurance, deductibles, and health savings account categories 332, 334, 336 representing the health care related financial terminology 206 of the overall data taxonomy 200.

Figure 4:
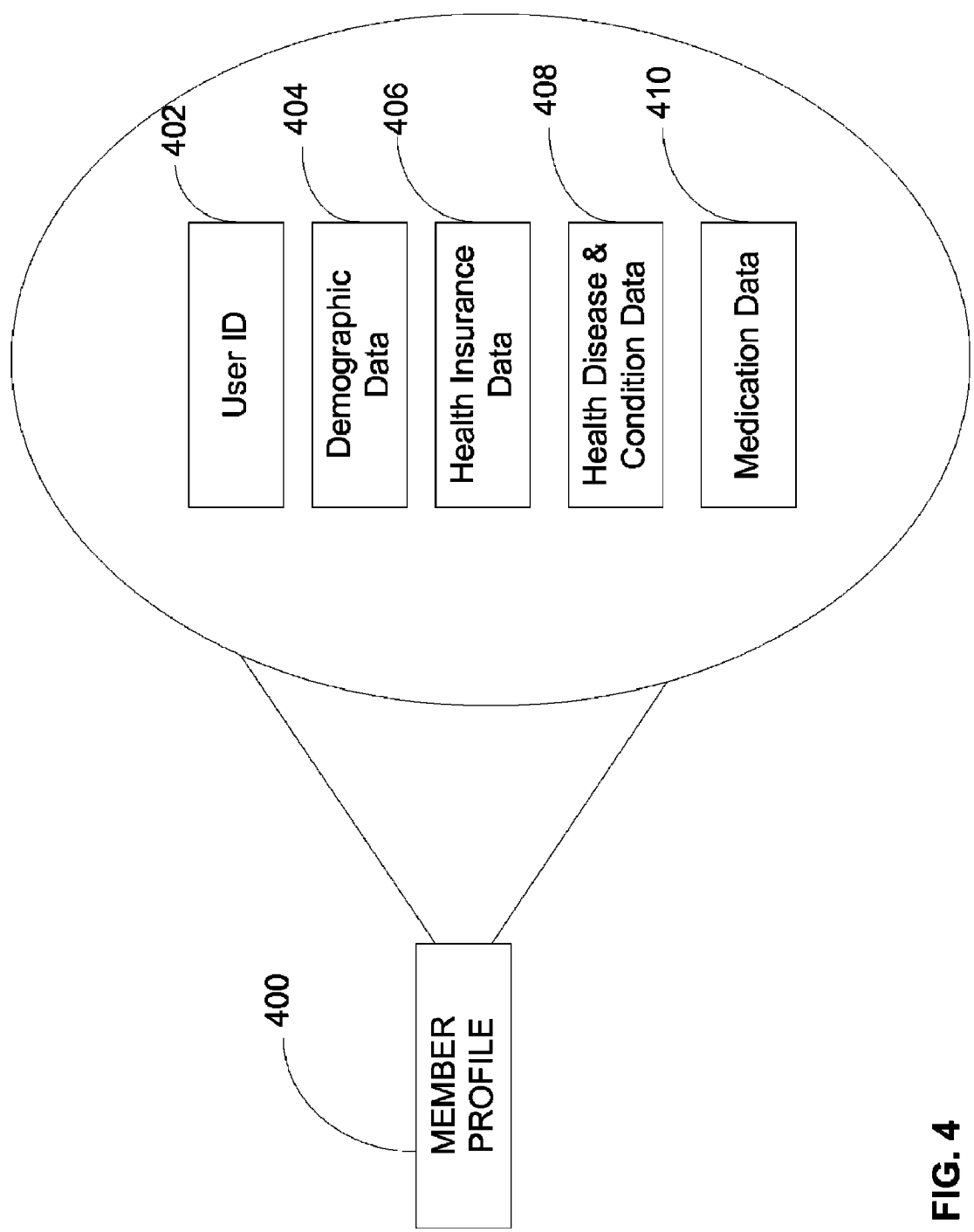
FIG. 4 is a diagram illustrating a member profile, in accordance with an embodiment of the invention.

As illustrated in FIG. 4, to put the overall health care data taxonomy 200 within the context of each member, the HCO 100 builds and dynamically updates a unique profile 400 for each member 102 by analyzing the continuously collected health care data 104, as well as tax-advantaged health care savings plan account data 136 specific to each member. Preferably, the member profile 400 is associated with each member 102 via a unique identifier 402, such as a user id. The member profile 400 comprises member-specific data, such as demographic data 404, member's health insurance data 406, member's health disease and condition data 408, and member's medication data 410. Preferably, the HCO 100 analyzes the member profile data 404-410 to determine a likelihood of the member 102 having one or more potential health conditions and stores an indicator associated with the identified potential health conditions in the member profile 400 for further assessment by a clinician and/or physician and, in one embodiment, for subsequent notification of the member 102 via the online interactive visual interface 106 or otherwise.

In an embodiment, the member demographic data 404 includes member's gender, date of birth, ethnicity, zip code, and plan sponsor information. The health insurance data 406 includes member's plan name and products included within the plan, such as medical, pharmacy, and Health Savings Accounts (HSA), for example. The health insurance data 406 collected in the member profile 400 further includes a plan sponsor presentation profile that specifies a partial list of topics to be displayed when the member logs into the online interactive visual interface 106 (FIG. 1). In embodiments, such topics may include one or more of mail order pharmacy information, disease management program information, such as diabetes management and weight management, information from the member's personal health record (PHR), as well as links to various diet, exercise, and disease management support tools. The health insurance data 406 further includes member's recent claim information, such as prescription, diagnostic tests, surgical center, and provider visit claims, for example. Finally, the health insurance data 406 includes the member's current health benefit amounts, such as the remaining deductible and coinsurance balances, as well as the member's health spending account balance information.

The member's health disease and condition data 408 accumulates self-reported conditions identified based on the information collected from the member's PHR, as well as health conditions and diseases identified based on the claims data. For example, the health condition data 408 may include flags indicating the likelihood of the member potentially having Type II diabetes and high cholesterol based on the analyzed provider and/or diagnostic test claim data, as well as flags indicating that a member suffers from high blood pressure and overweight conditions based on the information the member or the system reported via the PHR. In embodiments, the health disease and condition data 408 also includes one or more of the member's allergies, past diseases and conditions data (self-reported via the PHR, such as exposure to secondary smoke, or flagged based on analyzed historical claim data), date of most recent routine physical examination, member's vaccination status, as well as historical information on various health events, such as past surgical procedures, diagnostic tests, and the like. In an embodiment, if a potential condition, disease, or a health risk is flagged pursuant to the analysis of claim, diagnostic test, and medication data, clinicians associated with the HCO 100 further analyze the flagged data and, if appropriate, notify the member 102 and/or the member's physician. Finally, the member medication data 410 includes the member's prescription and over-the-counter drug purchase history. In an embodiment, the HCO 100 analyzes the medication data 410 to identify instances of potential savings, stores a corresponding indicator in the member profile 400, and notifies the member, via the online interactive visual interface 106, that generic medication information is available from the member's physician. In a further embodiment, the HCO 100 analyzes the medication data 410 to identify potential drug interactions, stores a corresponding indicator in the member profile 400, and notifies the member and his or her physician pursuant to a clinician's review.

Figure 5:
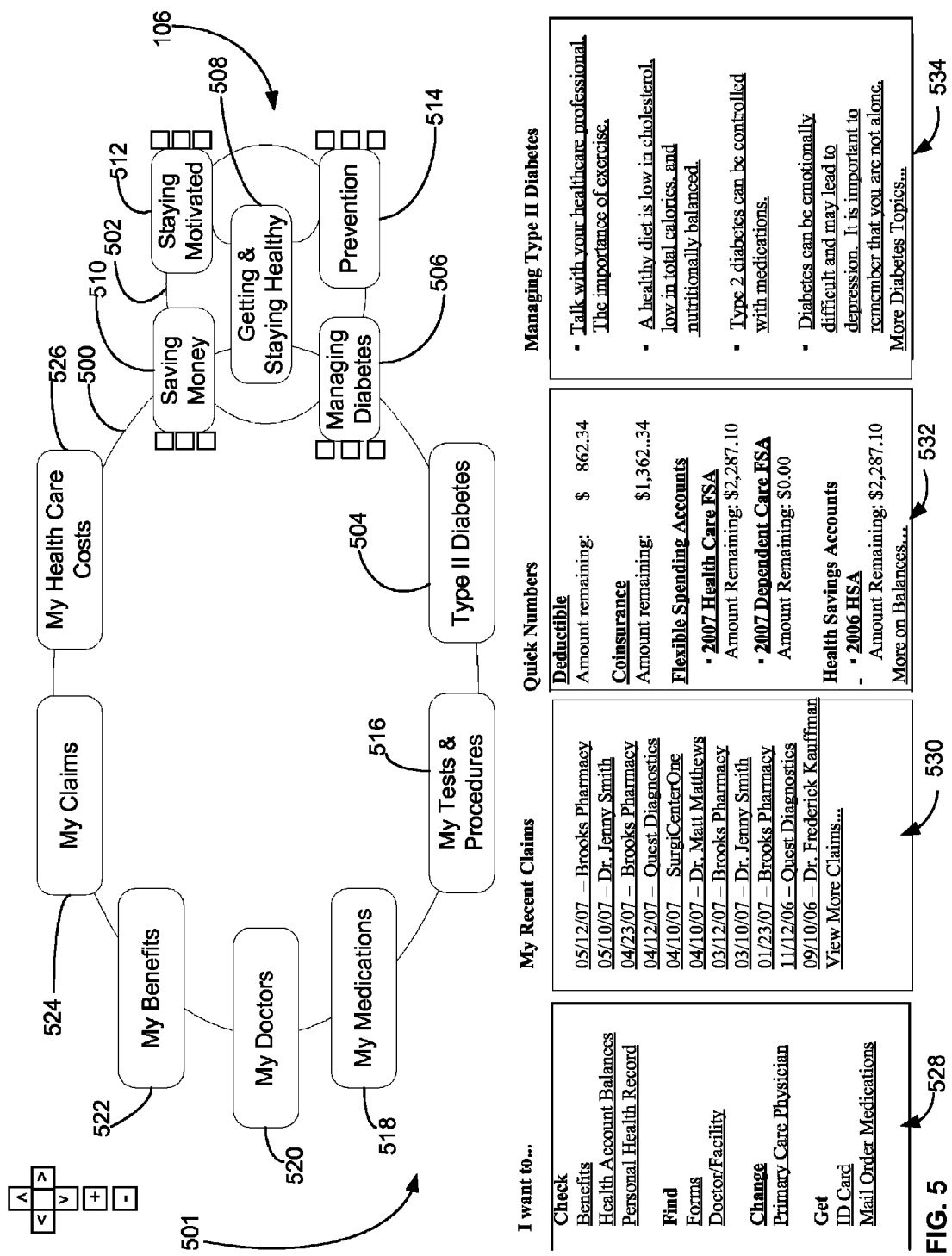
FIGS. 5-7 are diagrams illustrating an interactive online member interface comprising a custom category node display of member health care information based on analysis of the member profile of FIG. 4 in light of the overall health care data taxonomy of FIGS. 2 and 3, in accordance with an embodiment of the invention.

To empower the member 102 to make informed health care decisions, the HCO 100 graphically presents the member 102 with a manageable closed universe of health care data and information via the online interactive visual interface 106. Turning to FIG. 5, the online interactive interface 106 comprises a custom category node display of member health care data based on analyzing the member profile 400 in light of the overall health care data taxonomy 200. Preferably, upon receiving member login information, the HCO 100 identifies the member via the userid 402 (in combination with a password) and analyzes the corresponding member profile 400 to identify relevant health data categories among the plurality of health care data categories of the overall data taxonomy 200. Upon identifying the subset of relevant health care data categories within the data taxonomy 200, the HCO 100 initiates the display of the identified categories by way of a dynamically linked category node interface 106. In embodiments, the HCO 100 displays at least some of the relevant categories of the health care data taxonomy 200 directly, such as the Managing Diabetes category node 506 and the Type II Diabetes node 504 (corresponding to categories 313 and 312, respectively, of the overall taxonomy 200 illustrated in FIG. 3), while creating custom groupings of other relevant categories, such as the Account Balances subcategory node 706 discussed in more detail in connection with FIG. 7 below.

Upon member login into the online interactive visual interface 106, the HCO 100 identifies the health care data categories of the data taxonomy 200 that are relevant to the member 102 by performing one or more of the following analyses of the member profile 400: (a) analysis of the health conditions and medications data for diagnosed, as well as potential health risks and/or conditions, (b) analysis of claims for potential cost savings, such as through identifying whether a purchase of generic prescriptions and/or taking advantage of mail order pharmacy services may reduce the member's out-of-pocket costs, as well as identifying potential cost saving opportunities by suggesting selection of in-network providers and facilities instead of out-of-network options, (c) identification of relevant HCO programs and resources, which the member is not currently taking advantage of, (d) identification of relevant health content data that needs to be presented to the member, and (e) financial analysis of the member profile 400 to identify and suggest best use of member's benefits, as well as provide suggestions to reduce the member's health-based financial risk (for example, by suggesting an increase in the member's contribution to a tax-advantaged health care savings plan).

Once identified, the relevant health care category nodes are displayed for the member 102 as an interactive visual category node map, wherein related category nodes are interconnected by wireframes 500 to enhance the member's understanding of the relationships between the nodes and to provide a navigational aid with respect to the member's current position within the universe of his or her health care data. To enhance the member's understanding of the relationships between the category nodes, the HCO 100 preferably employs a ring node topology by displaying the interface 106 as a closed network or map, such as by locating each category node along one or more closed, loop-shaped wireframes 500, 502, which connect the interrelated categories. Preferably, HCO 100 initiates the display of the visual interface or map 106 by expanding one of the category nodes into related subcategories displayed on a separate intersecting wireframe 502. In this embodiment, the interface 106 is initialized by expanding the Getting & Staying Healthy node 508, along a separate wireframe 502, into related subcategories of Saving Money 510, Staying Motivated 512, Prevention 514, and Managing Diabetes 506.

FIG. 5 illustrates a "home page" 501 displayed upon initial member login. The home page 501 includes an initial display of the interface 106 for a member 102 having an indicator associated with type II diabetes included in his or her member profile 400. Therefore, pursuant to the analysis of the member profile 400, the HCO 100 customizes the display of the map/interface 106 by including a Type II Diabetes category node 504 and a Managing Diabetes category node 506. In the illustrated embodiment, the Managing Diabetes category node 506 inherits the corresponding subcategory structure 314-317, 319 identified in the overall data taxonomy 200 (FIG. 3). Additional health category nodes displayed via the interactive interface 106 categorize the rest of the health care information specific to the member 102 and include My Tests & Procedures 516, My Medications 518, My Doctors 520, My Benefits 522, My claims 524, and My Health Care Costs 526.

Preferably, the home page 501 further comprises a plurality of hyperlinks and text areas, providing the member 102 with links for taking health care management actions 528, viewing recent claim information 530, viewing deductible, coinsurance, and tax-advantaged health savings account balances 532, and displaying links 534 to additional information associated with one or more of the member's conditions or diseases (e.g., the Managing Type II Diabetes category node 506).

Figure 6:
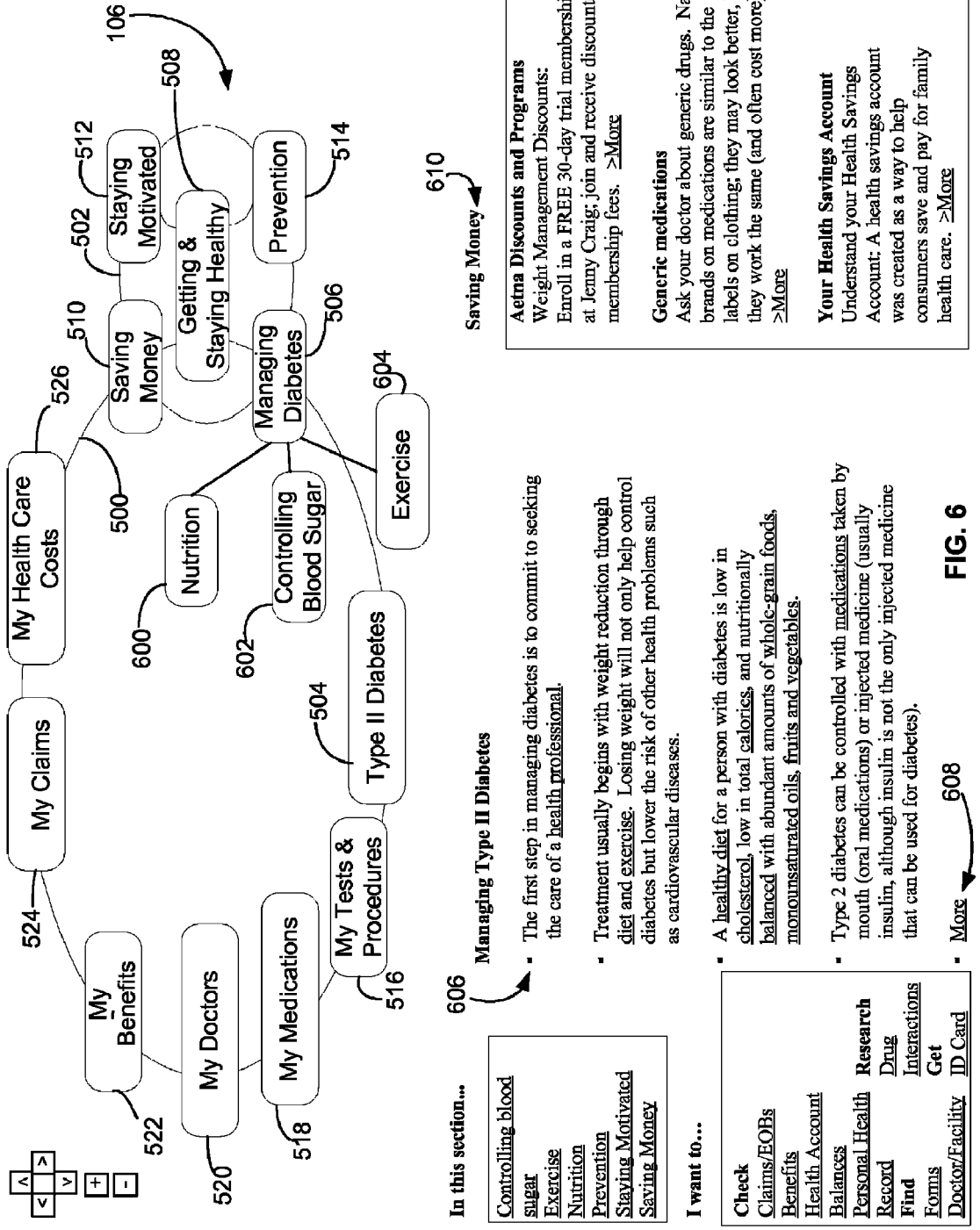

As shown in FIG. 6, the member 102 expands the logical display of at least one of the health care category nodes 504-526 into one or more related subcategory nodes, such as by using a pointing device (e.g., a mouse, a stylus or a finger in case of a mobile touch screen display) to click on/select and expand a category node. For example, as discussed above, the Managing Diabetes category node 506 inherits the corresponding subcategory structure 314-317, 319 identified in the overall data taxonomy 200 (FIG. 3). Therefore, upon member selection of the Managing Diabetes category node 506, the interactive visual interface 106 expands this category into Nutrition, Controlling Blood Sugar, and Exercise subcategory nodes 600-604, which correspond, either directly or via additional mapping, to the subcategory structure 315, 317, 319 of the overall data taxonomy 200 (FIG. 3). Since the member 102 selected a new category 506, the online display is updated with additional text and hyperlink information on the selected category 506 (e.g., Managing Type II Diabetes text area 606, including one or more hyperlinks 608). To further suggest related health care categories for exploration, the member 102 is presented with additional text areas corresponding to health care category nodes closely related to the current node selection, such as the Saving Money text area 610 associated with a health care category node 510. In this embodiment, the Saving Money text area 610 provides hyperlinks to additional information on discount programs, generic medication, and tax-advantaged savings accounts to enable the member 102 to gain financial control over expenses associated with the selected condition or disease (type II diabetes, in this example).

Figure 7:
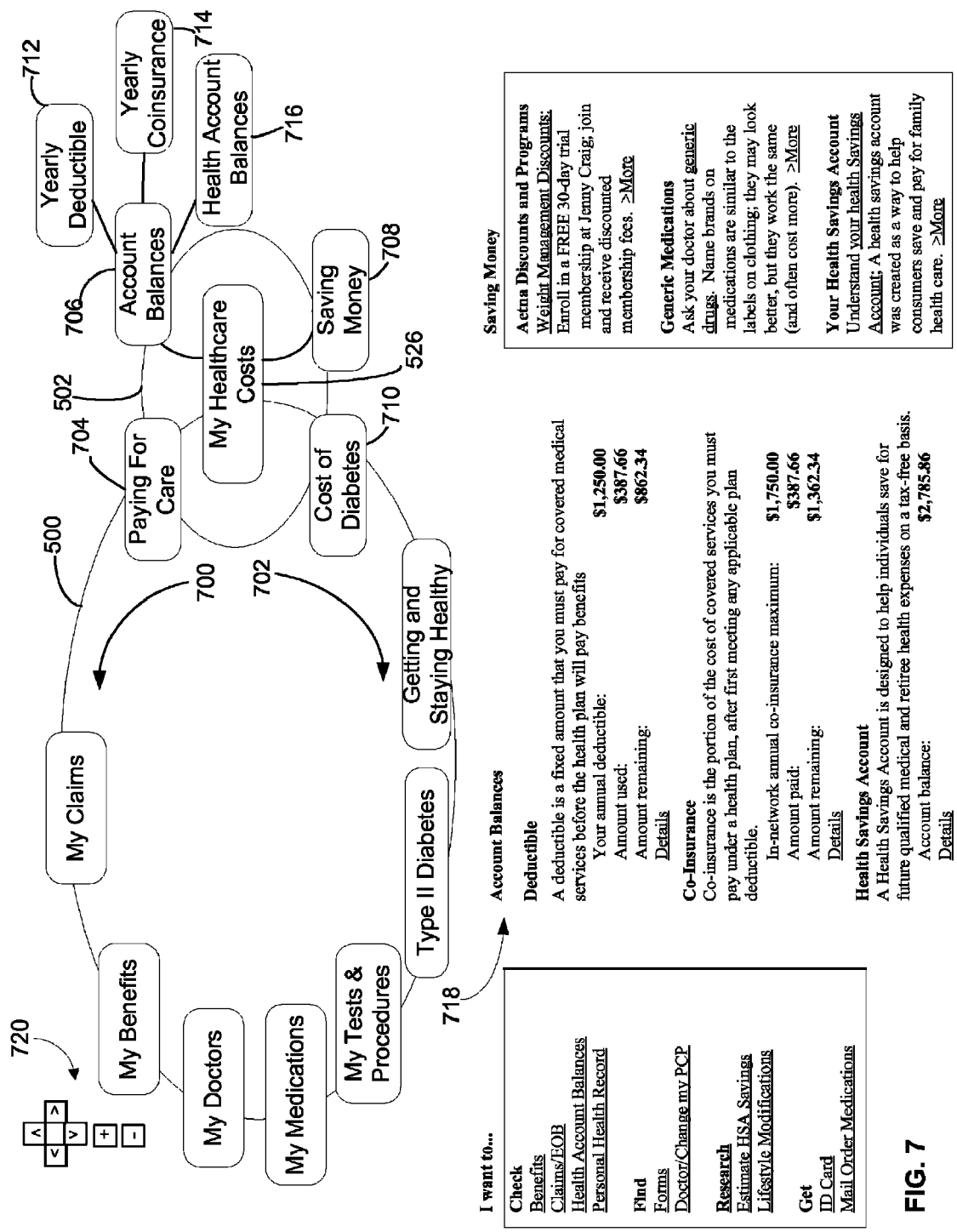

The online interface 106 also responds to member selection of a category node by reorienting the ring node topology display around the newly selected category, as shown in FIG. 7. In one embodiment, when the newly selected health care category includes additional subcategories, the interface 106 also expands the related subcategories along a separate ring wireframe. In this embodiment, the member 102 selected the My Health Care Costs node 526. Therefore, in order to orient the ring node topology display around the selected node 526, the interface 106 rotates all category nodes along the wireframe 500 in the direction 700 or 702. Preferably, the interface 106 reorients the node topology display so as to allow room for further expansion of the selected node 526 into its associated subcategory nodes 704-710 along an intersecting closed loop wireframe 502. In the illustrated embodiment, when the member 102 further selects one of the subcategory nodes 706 (Account Balances), presented along a separate wireframe 502, the interface 106 expands the selected node into further subcategories. In this case, the selected subcategory node 706 is expanded into further subcategories, entitled Yearly Deductibles 712, Yearly Coinsurance 714, and Health Account Balances 716 and corresponding to Deductibles 334, Coinsurance 332, and Health Savings Account 336 of the overall health care data taxonomy 200 (FIG. 3). In this embodiment, upon member login, the HCO 100 processes and updates the member profile 400 to identify one or more health conditions or diseases, filters the data taxonomy 200 in light of the member profile 400, and creates one or more custom groupings of a selected subset of health care categories for display via the interactive online interface 106. For example, the HCO 100 groups the Yearly Deductible, Yearly Coinsurance, and Health Account Balances categories 712-716 into a custom category entitled Account Balances 706. Since the member 102 selected the Account Balances category node 706, the display is updated with corresponding text information 718. In one embodiment, the member 102 also navigates the interactive display 106 via navigation controls 720, such as by panning the category display and/or zooming in or out of the category/subcategory node levels.

Figure 8:
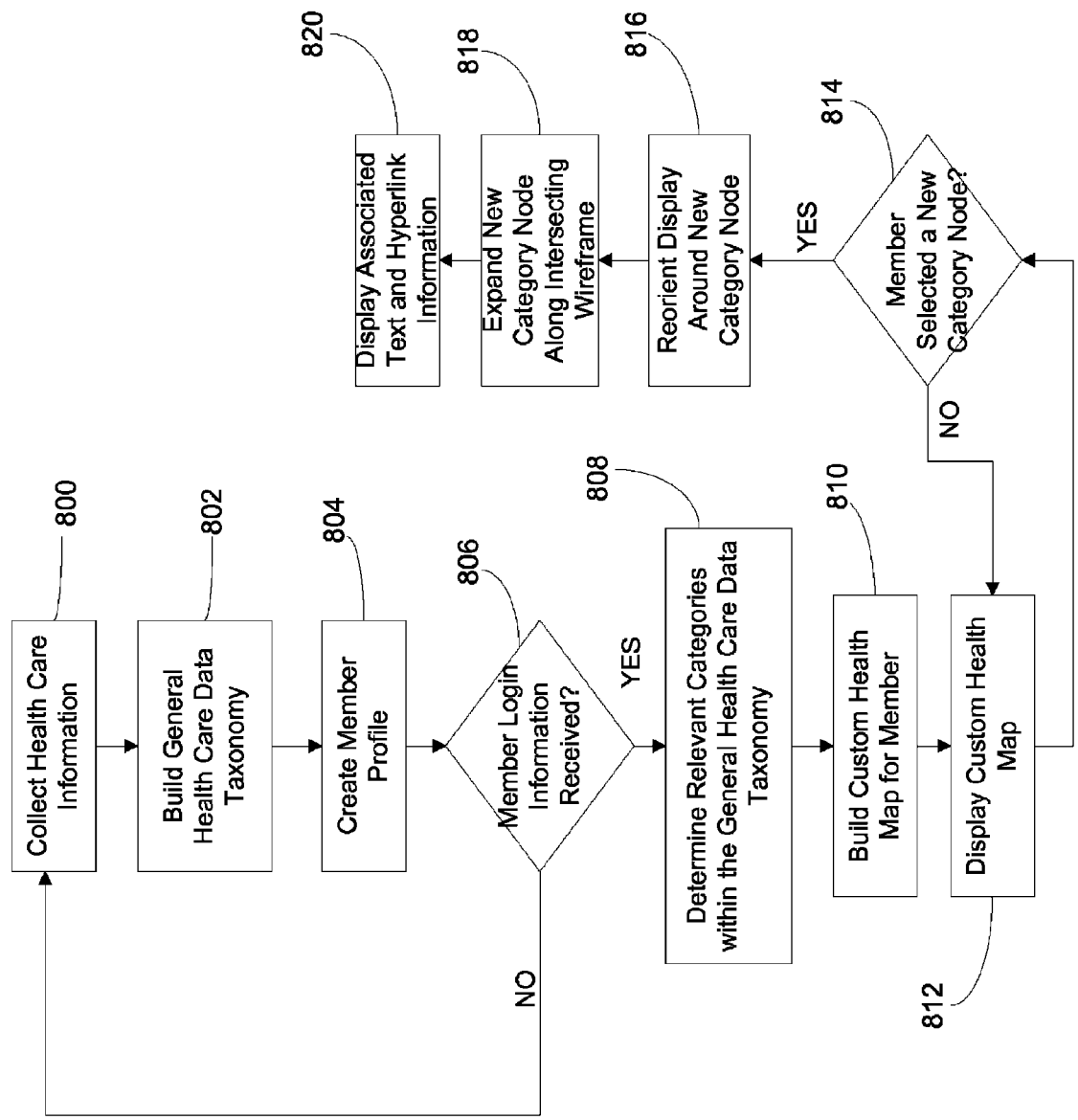
FIG. 8 is a flow diagram of a method for graphically representing a subset of a plurality of health care data categories of the health care data taxonomy of FIGS. 2 and 3 via an online health care category node map of FIGS. 5-7, in accordance with an embodiment of the invention.

Turning to FIG. 8, an embodiment of a method for graphically representing a subset of a plurality of health care data categories of health care data taxonomy via an online health care category node map is shown. In steps 800-804, the HCO 100 collects the health care information 104 in order to build the general health care data taxonomy 200 and to create and continuously update the member profile 400. The HCO 100 processes the member profile 400 to indicate the likelihood of the member 102 having one or more potential conditions, diseases, and health risks based on the claims, medication, and self-reported member data, among other factors. Furthermore, in an embodiment, the HCO 100 detects physician diagnoses within the member profile 400. If, in step 806, the HCO 100 receives member login information, it dynamically updates the member profile 400 and identifies a subset of relevant health data categories within the overall health care data taxonomy 200 based on the member profile, step 808. In an embodiment, the HCO 100 creates custom groupings of categories based on the identified subset of categories from the overall health care data taxonomy 200. In steps 810, 812, the HCO 100 builds and displays a custom health category map, presented via an online interactive interface 106, for the member 102. To enhance the member's understanding of the relationships between the category nodes, the HCO 100 preferably employs a ring node topology by displaying the interface 106 as a closed network or map, such as by locating each category node along one or more closed, loop-shaped wireframes 500, 502, which connect the interrelated categories. In embodiments, the HCO 100 displays the custom health category map via a computer, a mobile phone, a PDA, or another network-aware wired or wireless communication device available to the member 102. When, in step 814, the member 102 selects a new category node, the interface 106 reorients 816 the node map display around the newly selected category node. In one embodiment, the interactive interface 106 also expands the newly selected category node into one or more related subcategories along an intersecting loop-shaped wireframe 502 and displays additional text and hyperlink information associated with the newly selected health category, steps 818, 820.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for graphically representing a subset of a plurality of health care data categories to a health care plan member via an online health care category node map, the method comprising:
    building a health care data taxonomy relating health care terminology to one or more of health care benefits terminology, health care-related financial terminology, health insurance terminology, and dental insurance terminology;
    building and dynamically updating a member profile for the health care plan member;
    storing the health care data taxonomy and the member profile in a database;
    receiving, via a network, an online member identification token associated with the health care plan member;
    identifying the subset of the plurality of health care data categories based on correlating the health care data taxonomy with the member profile corresponding to the online member identification token;
    initiating a display of the online health care category node map, the display comprising a ring node topology of health care category nodes disposed along a loop-shaped wireframe structure for graphically indicating a relationship between adjacent health care category nodes within the subset, the online health care category node map responding to member input that selects a category node by orienting the ring node topology display around the selected category node by way of automatically rotating the health care category nodes along the loop-shaped wireframe structure so as to accommodate expansion of the selected category node into subcategories; and
    wherein at least one category node in the online health care category node map comprises one or more subnodes corresponding to one or more health care data subcategories, the at least one category node of expanding into the one or more subnodes responsive to member input that selects the at least one category node.

2. The method of claim 1 further comprising displaying text corresponding to content associated with the selected category node.

3. The method of claim 1 further comprising displaying one or more hyperlinks to content associated with the one or more subnodes.

4. The method of claim 1 wherein the member profile comprises at least one of member demographic data, diagnosis data, claims data, health care plan benefits data, health diseases and conditions data, medication data, health event data, allergy data, and vaccination data.

5. The method of claim 4 further comprising collecting at least one of the member demographic data, health diseases and conditions data, medications data, health event data, allergy data, and vaccination data based on information reported by the member.

6. The method of claim 4 wherein building the member profile further comprises analyzing one or more of the member demographic data, claims data, diagnosis data, medication data, health event data, and member-reported health conditions to determine a likelihood of the member having one or more potential health conditions and storing an indicator associated with the one or more potential health conditions in the member profile.

7. The method of claim 4 further comprising deriving the medication data from at least one of member-reported medication data and pharmacy claims data.

8. The method of claim 5 further comprising interfacing with a personal health record application to obtain the information reported by the member.

9. A non-transitory computer readable medium having stored thereon computer executable instructions for graphically representing a subset of a plurality of health care data categories to a health care plan member via an online health care category node map, the instructions comprising:
    building a health care data taxonomy relating health care terminology to one or more of health care benefits terminology, health care-related financial terminology, health insurance terminology, and dental insurance terminology;
    building and dynamically updating a member profile for the health care plan member;
    storing the health care data taxonomy and the member profile in a database;
    receiving an online member identification token associated with the health care plan member;
    identifying the subset of the plurality of health care data categories based on correlating the health care data taxonomy with the member profile corresponding to the online member identification token;
    initiating a display of the online health care category node map, the display comprising a ring node topology of health care category nodes disposed along a loop-shaped wireframe structure for graphically indicating a relationship between adjacent health care category nodes within the subset, the online health care category node map responding to member input that selects a category node by orienting the ring node topology display around the selected category node by way of automatically rotating the health care category nodes along the loop-shaped wireframe structure so as to accommodate expansion of the selected category node into subcategories; and
    wherein at least one category node in the online health care category node map comprises one or more subnodes corresponding to one or more health care data subcategories, the at least one category node expanding into the one or more subnodes responsive to member input that selects the at least one category node.

10. The computer readable medium of claim 9 further comprising instructions for displaying text corresponding to content associated with the selected category node.

11. The computer readable medium of claim 9 further comprising instructions for displaying one or more hyperlinks to content associated with the one or more subnodes.

12. The computer readable medium of claim 9 wherein the member profile comprises at least one of member demographic data, diagnosis data, claims data, health care plan benefits data, health diseases and conditions data, medication data, health event data, allergy data, and vaccination data.

13. The computer readable medium of claim 12 further comprising instructions for collecting at least one of the member demographic data, health diseases and conditions data, medications data, health event data, allergy data, and vaccination data based on information reported by the member.

14. The computer readable medium of claim 12 wherein the instructions for building the member profile further comprise analyzing one or more of the member demographic data, claims data, diagnosis data, medication data, health event data, and member-reported health conditions to determine a likelihood of the member having one or more potential health conditions and storing an indicator associated with the one or more potential health conditions in the member profile.

15. A system for graphically representing a subset of a plurality of health care data categories to a health care plan member via an online health care category node map, the system comprising:

a database for storing (a) a health care data taxonomy relating health care terminology to one or more of health care benefits terminology, health care-related financial terminology, health insurance terminology, and dental insurance terminology, and (b) a dynamic member profile for the health care plan member;

a server for initiating a display of the online health care category node map, the server comprising memory having stored thereon computer executable instructions for:

receiving an online member identification token associated with the health care plan member;

identifying the subset of the plurality of health care data categories based on correlating the health care data taxonomy with the member profile corresponding to the online member identification token;

initiating the display of the online health care category node map, the display comprising a ring node topology of health care category nodes disposed along a loop-shaped wireframe structure for graphically indicating a relationship between adjacent health care category nodes within the subset, the online health care category node map responding to member input that selects a category node by orienting the ring node topology display around the selected category node by way of automatically rotating the health care category nodes along the loop-shaped wireframe structure so as to accommodate expansion of the selected category node into subcategories; and wherein at least one category node in the online health care category node map comprises one or more subnodes corresponding to one or more health care data subcategories, the at least one category node expanding into the one or more subnodes responsive to member input that selects the at least one category node.

16. The system of claim 15 wherein the memory further comprises instructions for displaying text corresponding to content associated with the selected category node.

17. The system of claim 15 wherein the memory further comprises instructions for displaying one or more hyperlinks to content associated with the one or more subnodes.

18. The system of claim 15 wherein the dynamic member profile comprises at least one of member demographic data, diagnosis data, claims data, health care plan benefits data, health diseases and conditions data, medication data, health event data, allergy data, and vaccination data.

19. The system of claim 18 wherein the memory further comprises instructions for collecting at least one of the member demographic data, health diseases and conditions data, medications data, health event data, allergy data, and vaccination data based on information reported by the member.

20. The system of claim 18 wherein the memory further comprises instructions for building the dynamic member profile by analyzing one or more of the member demographic data, claims data, diagnosis data, medication data, health event data, and member-reported health conditions to determine a likelihood of the member having one or more potential health conditions and storing an indicator associated with the one or more potential health conditions in the dynamic member profile.

* * * * *